United States Patent [19]

Bagaoisan et al.

[11] Patent Number: 5,893,867
[45] Date of Patent: Apr. 13, 1999

[54] STENT POSITIONING APPARATUS AND METHOD

[75] Inventors: Celso J. Bagaoisan, Union City; Gholam-Reza Zadno-Azizi, Newark; Jeffrey F. Field, Northridge, all of Calif.

[73] Assignee: Percusurge, Inc., Sunnyvale, Calif.

[21] Appl. No.: 08/744,632

[22] Filed: Nov. 6, 1996

[51] Int. Cl.[6] .................................................. A61M 29/00
[52] U.S. Cl. ................................. 606/198; 606/1; 623/1
[58] Field of Search ............................. 606/1, 108, 191, 606/194, 195, 198, 200; 623/1, 12; 29/234, 275, 282, 283

[56] References Cited

U.S. PATENT DOCUMENTS 5,188,616  2/1993  Nadal ...................................... 606/200
5,437,083  8/1995  Williams et al. .
5,626,604  5/1997  Cottone, Jr. ............................ 606/198

*Primary Examiner*—William Lewis
*Attorney, Agent, or Firm*—Knobbe, Martens Olson & Bear

[57] ABSTRACT

A stent positioning apparatus and method are provided for the attachment of a stent to a balloon to be used in the treatment of stenosis, such as coronary angioplasty. In one preferred embodiment, a first generally cylindrical member has a radially deformable wall defining a channel within which the stent and balloon assembly are inserted. A second generally cylindrical member has an opening sufficient to receive the first member with the assembly therein. The second member is then slid longitudinally over the deformable wall of the first member causing nonuniform depressions to be formed in the inner diameter of the stent, thus crimping the stent onto the balloon. Thus, the stent is attached to the balloon without damage and without risk of the stent falling off the balloon prematurely.

39 Claims, 8 Drawing Sheets

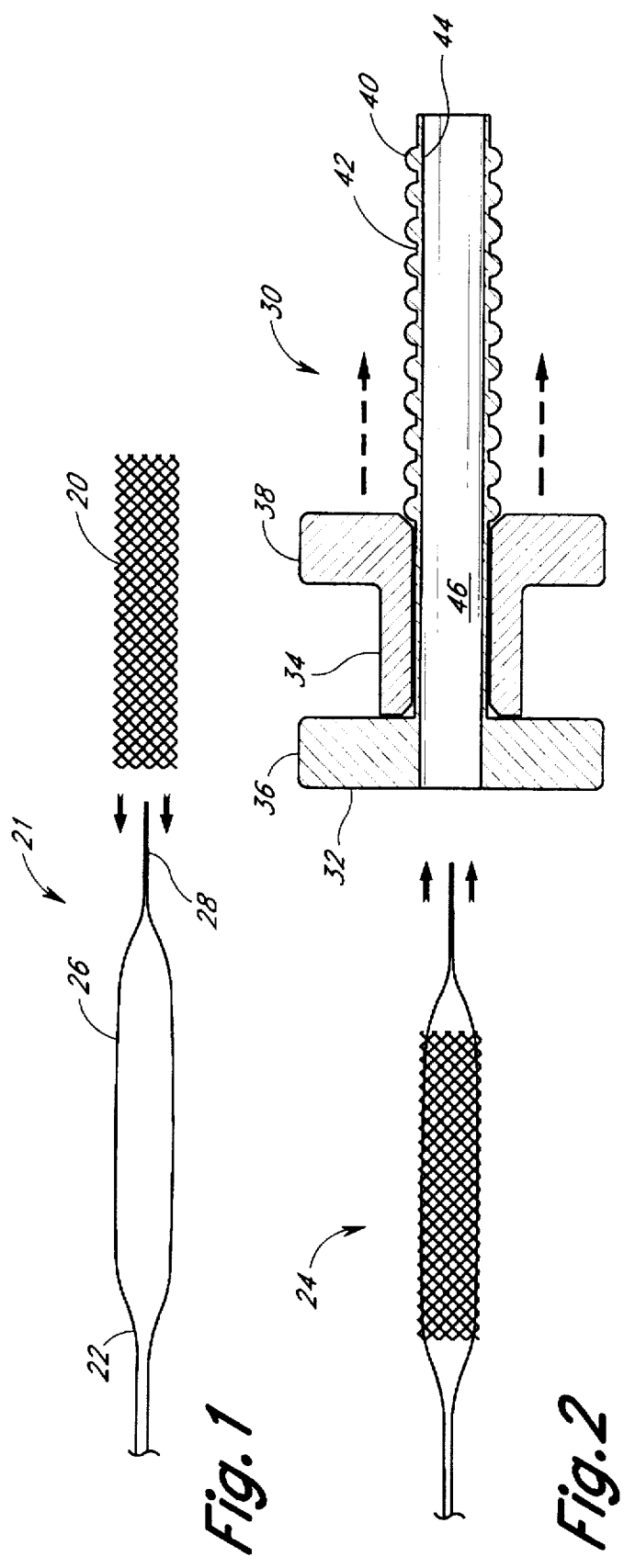

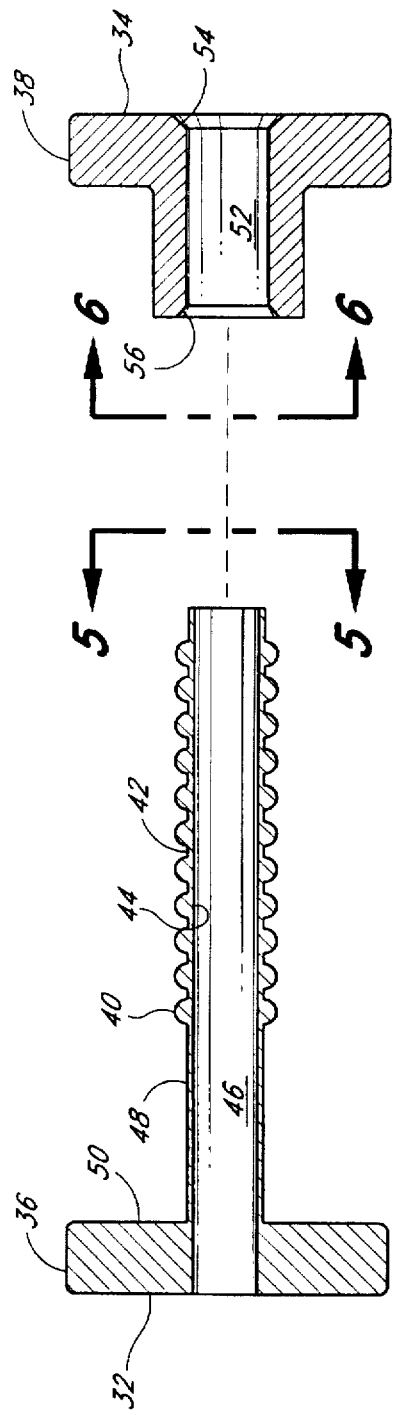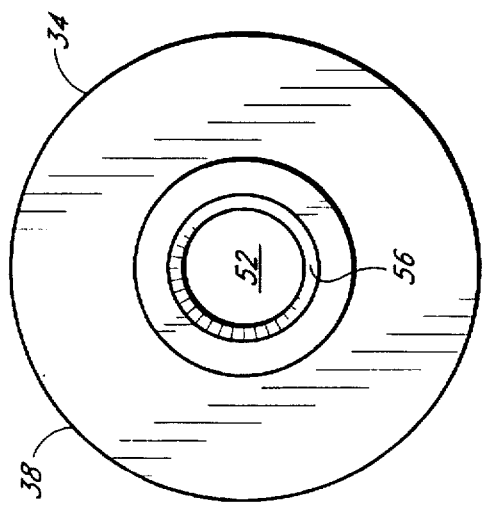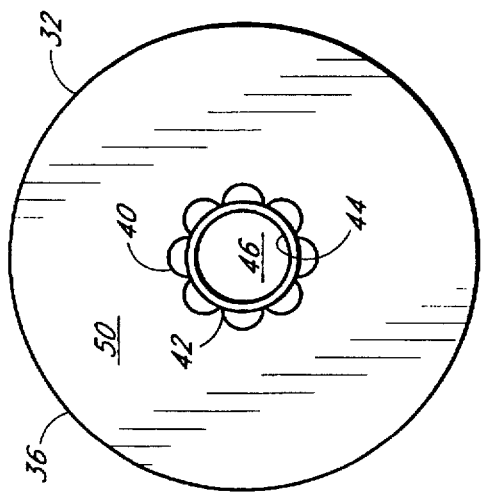

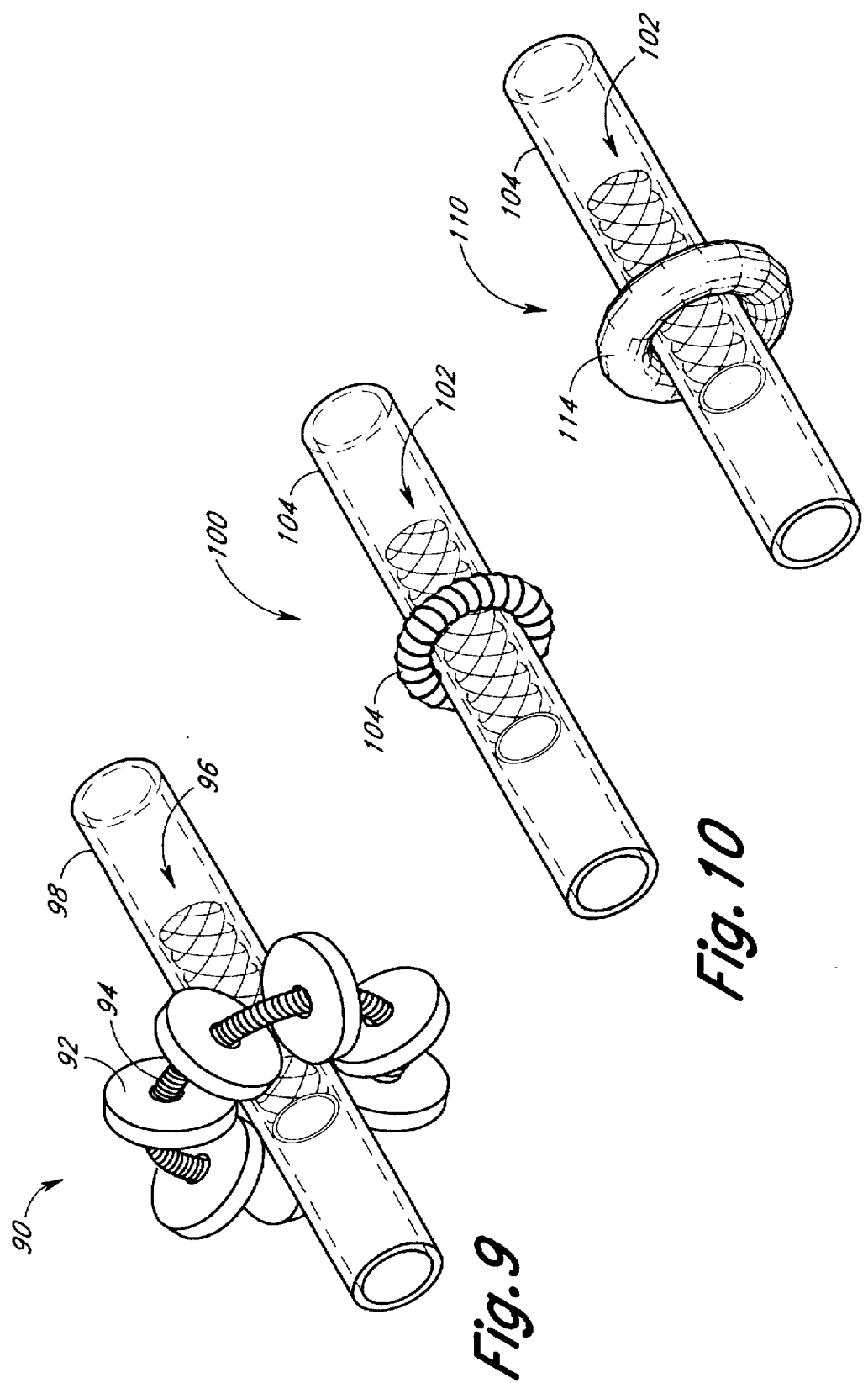

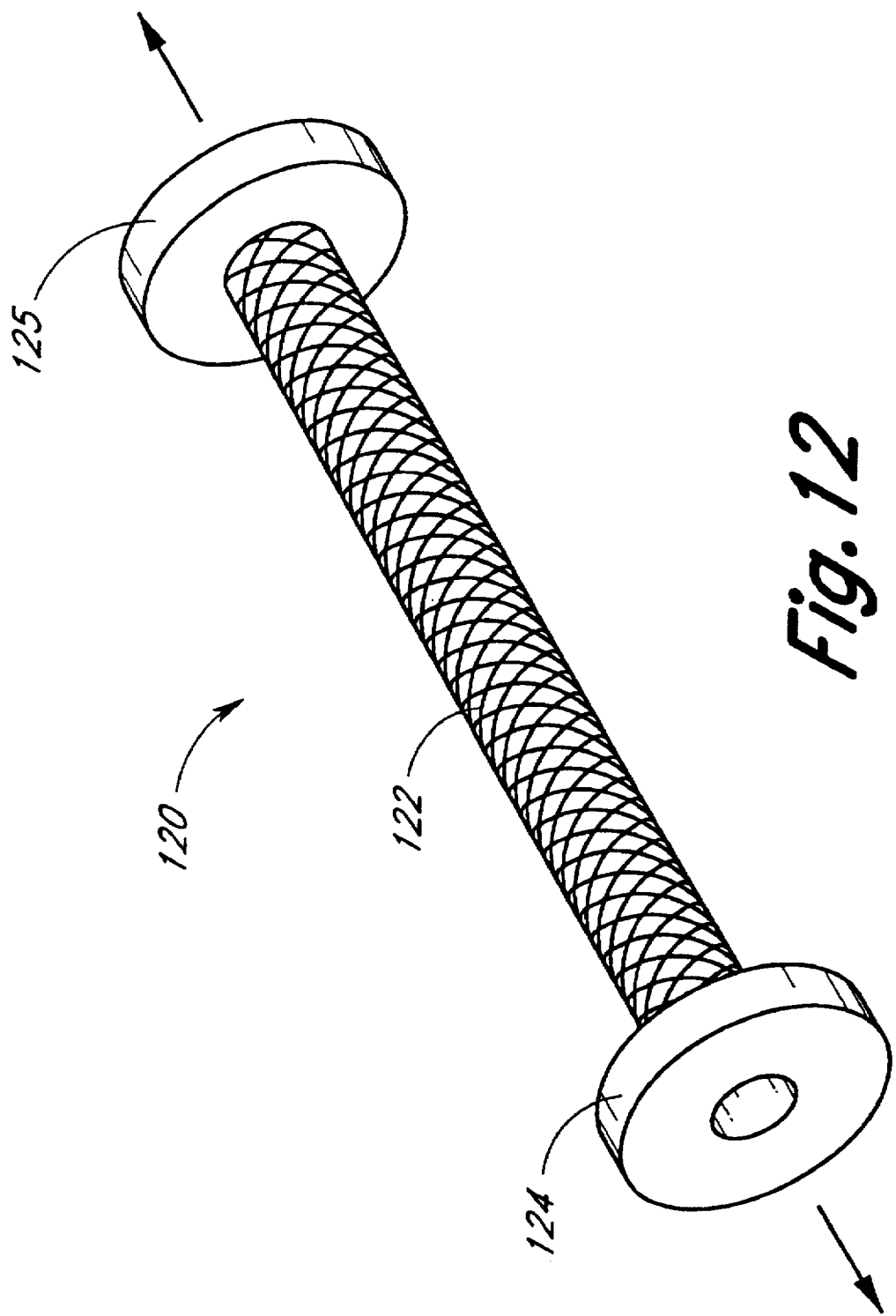

ns 1 STENT POSITIONING APPARATUS AND METHOD

FIELD OF THE INVENTION

The present invention relates generally to the field of stents and balloon catheters for medical use, and, in particular, to an apparatus and method for positioning or loading an unexpanded stent onto an uninflated balloon for insertion into a patient during a surgical procedure such as that typically referred to as percutaneous transluminal angioplasty (PTA).

BACKGROUND OF THE INVENTION

PTA is a common medical procedure used to widen a stenosis or constriction of the diameter of a bodily passage, such as an artery. When the procedure is applied to a coronary artery, it is referred to as percutaneous transluminal coronary angioplasty (PTCA); however, this procedure, as well as other similar medical procedures, may be applied to peripheral arteries, such as the carotid, or a wide variety of other vessels. It is common in such procedures to use a balloon delivery catheter in conjunction with an intravascular prosthesis or stent. One or more dilation balloons may be used to widen the artery at the point of occlusion, and a subsequent balloon is used to position the stent at the proper location. The balloon is inflated to expand the stent to its working diameter, and is sized (often by another balloon) to implant the stent into the vascular wall. Plastic deformation of the stent prevents it from collapsing once the balloon has been deflated and removed from the patient. The stent is typically metallic and may comprise stainless steel or tantalum, for example. Thus, restenosis is resisted by the stent.

In order to adequately attach the unexpanded stent onto the balloon catheter for delivery into the patient, without having the stent come off the balloon prematurely, the stent is "crimped" or otherwise radially collapsed sufficiently to attach it to the balloon. It is typical in some countries for this crimping to be performed manually by the physician in the catheter laboratory. However, there is the risk that too much or too little pressure may be applied and the balloon and/or stent may be damaged, lost, or may not otherwise perform as desired during the procedure. On the other hand, there is the opposite risk that the physician will not apply enough crimping pressure to the stent to load it onto the balloon, thus allowing it to slip or rotate on the catheter during deployment, or to come off entirely, leading to a possibly catastrophic result. Accordingly, in other countries, stents are required by regulation to be crimped onto their associated delivery balloon at the time of production by the manufacturer; such "preattached" stents enjoying the benefits of production quality control procedures.

This problem is addressed by U.S. Pat. No. 5,437,043 to Williams et al., which discloses a production stent-loading mechanism designed to automatically load a stent onto the distal end of a catheter assembly with a minimum of human handling, with the goal of more securely attaching the stent onto the catheter. In one embodiment of this mechanism, a tubular member with an inner inflatable bladder receives a balloon catheter having a stent positioned over the uninflated balloon. Inflation of the bladder causes an annular portion of the bladder surrounding the stent to crimp the stent onto the balloon. Assuming accurate calibration of the pressurization device, a uniform crimping pressure will be applied to the stent to secure it to the uninflated balloon. In other embodiments, plates moving relative to one another exert a similar uniform crimping pressure to the cylindrical exterior surface of the stent. Thus, in this device, if the maximum and minimum crimping pressures are not carefully regulated, the stent could either fall off or become damaged, respectively. Such precise pressure regulation undoubtedly adds greatly to the cost of stent/catheter production, not to mention the complexity of the mechanism itself. In addition, however, with such preattached stents, the physician's option to use alternate delivery balloons is severely restricted, as it is left completely to the discretion of the stent manufacturer.

Thus, in the absence of more secure manual loading mechanisms and methods, only preattached stents and balloon catheters are available for a physician's use in some countries. Although this may obviate the need for manual attachment by the physician, thus achieving a higher degree of safety, the physician no longer has the option to choose the most suitable balloon catheter and preferred stent for a particular patient's needs.

Therefore, there is a need for nonproduction stent loading devices and techniques which allow greater freedom and flexibility in stent and balloon catheter combinations, as well as for production devices which will more securely load a stent onto the catheter without requiring precise pressure regulation.

SUMMARY OF THE INVENTION

The stent loading apparatus and method of the present invention satisfies the need in the prior art by providing a mechanism for applying a nonuniform or noncontinuous crimping pressure to the stent. In this fashion, both longitudinal and rotational movement of the stent relative to the catheter are prevented. Thus, more secure attachment is, achieved without precise pressure regulation and with reduced risk of damage to the stent or the balloon catheter. Moreover, the apparatus and method of the present invention provide a mechanism which is simple, quick, and economical. In fact, in a preferred embodiment, the stent positioning apparatus is disposable. The physician thus has the opportunity to select a desired stent from a first manufacturer and a desired balloon catheter from a second manufacturer, as desired. The simplicity of use of the present invention allows an assistant to quickly prepare a stent-balloon assembly prior to or during the procedure. Thus, not only is the quality of care for the patient improved, but the spiraling costs of health care are reduced somewhat. Even for preattached stents, more secure attachment with reduced manufacturing precision translates into improved quality at less cost.

These advantages are achieved in the present invention by providing a mechanism which applies a crimping pressure to the stent such that nonuniform, noncontinuous depressions or deformations are formed on the exterior of the stent in order to secure it to the balloon catheter. These depressions or deformations result in negative craters (e.g., the absence of material) formed on the exterior surface of the stent, and further result in positive protrusions on the inner surface or inner diameter (ID) of the stent wall. By "nonuniform," it will be understood that, although the crimping pressure may or may not be uniform, it will not result in a stent with a uniformly reduced diameter. That is, the inner diameter of the stent will be less in some areas (e.g., in the areas corresponding to the locations of the depressions) than in other areas. Such areas of reduced ID serve to selectively secure the stent to the catheter and simultaneously, depending upon how they are arranged on the stent, prevent longitudinal and rotational movement thereof. By "noncontinuous," similarly, the depressions or deformations on the exterior surface of the stent are not continuously formed with respect to such surface, but occur only in selected locations thereon.

Thus, the depressions which result in these areas of reduced ID are preferably applied intermittently or preferentially around the cylindrical exterior surface of the stent. Such depressions can take the form of detents, inverted protuberances, bumps, bars, lines, or any number of configurations. What is unique to the present invention is that crimping pressure need only be applied in these areas, leaving the remainder of the stent (indeed, possibly the majority of the exterior surface) less crushed and more protected from damage. Thus, slightly increased and more secure crimping pressures may be selected without increasing the risk of damage to the stent.

A preferred embodiment of an apparatus having features of the present invention comprises a first member and a second member. The first member has a radially deformable wall defining a longitudinal channel within which a stent-balloon assembly comprising a selected unexpanded stent and uninflated balloon catheter are inserted. The second member has an opening sized to receive the first member with the stent-balloon assembly therein. Longitudinal movement of the second member over the first member causes the deformable wall to compress radially inward, thereby crimping the stent onto the balloon. In this embodiment, the crimping is achieved as follows.

A plurality of protuberances or bumps are formed on an exterior of the first member (or inner, forming member). A second generally cylindrical outer member (or pressure member) has an opening sufficient to receive the first member with the assembly therein. The second member is then slid longitudinally over the bumps of the first member applying a force or pressure to the inner member, thus causing the crimping of the stent onto the balloon. Thus, the protuberances on the inner member serve to apply a forming action or deformation on the exterior surface of the stent, the force for which is supplied by the outer or pressure member as it slides over the forming member. Alternatively, the protuberances may be formed in the interior surface of the forming member, such that they directly engage the stent. In addition, the forming and pressure members can be separate components as in the foregoing embodiment, or may be combined into an integral device.

In the preferred embodiment, flanges are provided on ends of the first and second members for easy grasping by the physician or assistant. The plurality of bumps are spaced longitudinally and circumferentially about the first member. The bumps may be rounded or frusto-conical in shape, or may comprise other configurations. The second member may alternatively comprise another shape, such as generally frusto-conical, without loss of the benefits and advantages of the present invention. The preferred materials for the first and second members, for example, are a thermoplastic elastomer, styrene-ethylene butadiene-styrene block co-polymer and a rigid thermoplastic, respectively.

In the method of the present invention, the stent is first positioned over the distal end of the deployment device, typically a balloon catheter. The stent-catheter combination is then positioned within a channel defined by the inner member. This inner member, as noted above, serves as a forming device since it is provided with some type of forming tools, such as protuberances, bumps, etc., which can be nonuniformly or noncontinuously spaced thereon. In the next step of the method, a forming pressure is applied to the forming member, thus deforming the stent in a crimping action to securely mount it on the deployment catheter. It will be noted that the forming pressure can be applied to the stent in a wide variety of ways while still achieving the benefits of the present invention. For example, a pliers-like tool may be used to provide radial compression of the stent onto the balloon catheter. Distal, mating ends of the tool form a channel of circular cross-section corresponding to the desired crimped diameter of the unexpanded stent.

In another preferred embodiment, an apparatus having features of the present invention may comprise a braided tube having flanges on its ends. Pulling the flanges in opposite directions will reduce the tube diameter, thereby radially compressing the stent and balloon assembly positioned in the tube.

The stent positioning apparatus and method of the present invention exhibits a number of important advantages vis-a-vis current stent design and construction. These topics are constantly undergoing intensive analysis and development; yet, the principles of the present invention are completely compatible with such trends. This provides a device which is flexible and versatile in use.

Important in stent design are issues of radial strength, gap size, strut thickness, thrombogenicity, and strut material. With regard to radial strength, a number of strut designs have been implemented. In one common stent, the struts or filaments are arrayed in a slotted configuration which, upon expansion, deploy as a mesh work of adjacent parallelograms. Other stents are formed in the shape of a coiled piece of wire, while others use a sinusoidal wire formed in a helical wrap. Still other stents are formed from wires which are loosely woven into broad loops. Each stent configuration is designed to achieve certain advantages in terms of radial strength, with the ultimate goal of avoiding restenosis.

Regardless of the stent design, the noncontinuous distribution of the crimping detents formed in the stent by the apparatus and method of the present invention are sufficient to provide secure attachment to the deployment device. Likewise, whether the stent is constructed from a flat or round wire, the present invention is equally applicable. The protuberances can be formed from a variety of shapes in order to deform portions of the struts sufficiently for crimping purposes.

The gap size of stents is sometimes analyzed in terms of the ratio between the open space between struts to the metal surface area. Because of the way that the protuberances on the forming member are selectively placed thereon, sufficient deformation of the struts is ensured (i.e., not all protuberances will engage in an open-space area). Thrombogenicity is the tendency of the stent to produce clots or thrombi. Substantial research and development is being conducted with respect to the material for constructing the stent in order to minimize thrombogenicity. Thus, nonmetallic materials, such as PET, are being investigated. Also, coatings are sometimes utilized to minimize thrombogenicity and decrease the percentage of restenosis.

In all of these efforts, the present invention is compatible. Because the stent is deformed in only selected and localized positions, the scientific advantages hoped to be achieved from the stent material are largely left intact through the attachment process. Moreover, there is a trend toward shorter stents, e.g., less than 15 millimeters. Thus, the advantages of the present invention are even more significant in order to provide secure positioning on the deployment device. Some stents are provided with an articulated region to facilitate bending or flexing. In accordance with one advantage of the present invention, the forming protuberances can be distributed on the forming device so as to avoid sensitive areas, such as these, or where the gold or platinum rings are formed on the stent for visualization purposes.

Although forming protuberances are illustrated in connection with the present invention, it will be understood that it is not limited to noncontinuous stent mounting. Various embodiments of manual stent attachment devices are illustrated in the drawings and described below. Such devices can be utilized with uniform, as well as nonuniform, crimping or forming mechanisms. Likewise, although the principles of the present invention are illustrated in terms of manual attachment devices, they are equally applicable, and readily adaptable by one of ordinary skill, to nonmanual or production attachment systems.

As noted above, the present stent positioning apparatus and method provide an important advantage in the opportunity to selectively combine the stent and balloon catheter the physician wishes to use. The various embodiments also provide another important advantage of the present invention which is the simplicity and ease with which the stent is satisfactorily attached to the balloon catheter.

Thus, the present invention advantageously comprises an apparatus for securing any therapeutic device, such as an angioplasty stent, and the like, onto the distal end of a suitable deployment device, such as a balloon catheter, and the like, wherein said apparatus comprises a first member defining a channel along its longitudinal axis, the channel having a diameter greater than the diameter of said therapeutic device such that said device and said deployment device are positionable within the channel; and further comprising a second member having an opening for receiving the first member, said second member applying a crimping pressure on said first member such that said first member reduces the inner diameter of said therapeutic device nonuniformly without damage to either said therapeutic or deployment devices, thereby securing said therapeutic device onto said deployment device. The present invention further comprises an apparatus having an inner member comprising a channel and at least one forming member placed on said inner member, said channel being dimensioned to receive a therapeutic device, and further comprising a pressure member for applying a crimping pressure on said forming member to selectively reduce the inner diameter of said therapeutic device non-uniformly and without damage thereto, thereby crimping said therapeutic device onto an appropriate deployment device. Furthermore, the present invention encompasses a method comprising the steps of positioning a therapeutic device over an appropriate deployment device, providing a plurality of forming members so as to be adjacent the therapeutic device, and applying a force to the forming members to cause them to engage the therapeutic device and selectively deform such device so that it engages the deployment device in a crimping manner.

Further advantages and applications will become apparent to those skilled in the art from the following detailed description of the preferred embodiments and the drawings referenced herein, the invention not being limited to any particular embodiment.

BRIEF DESCRIPTION OF THE DRAWINGS

FIG. 1 shows an exploded view of an unexpanded stent to be positioned over the distal end of an uninflated balloon delivery catheter;

FIG. 2 shows an assembly comprising the stent and balloon catheter prior to insertion into a preferred embodiment of a stent positioning apparatus of the present invention comprising an inner member and an outer member, where the apparatus is shown in longitudinal cross-section;

FIG. 3 shows a detailed, longitudinal cross-sectional view of the apparatus and assembly after radial compression of the inner member by the outer member;

FIG. 4 shows an exploded view of the apparatus of FIG. 3;

FIG. 5 shows an end view taken along lines 5—5 of FIG. 4;

FIG. 6 shows an end view taken along lines 6—6 of FIG. 4;

FIGS. 7–13 show perspective views of alternative embodiments of an apparatus having features of the present invention.

DETAILED DESCRIPTION OF THE PREFERRED EMBODIMENTS

Figure 7:
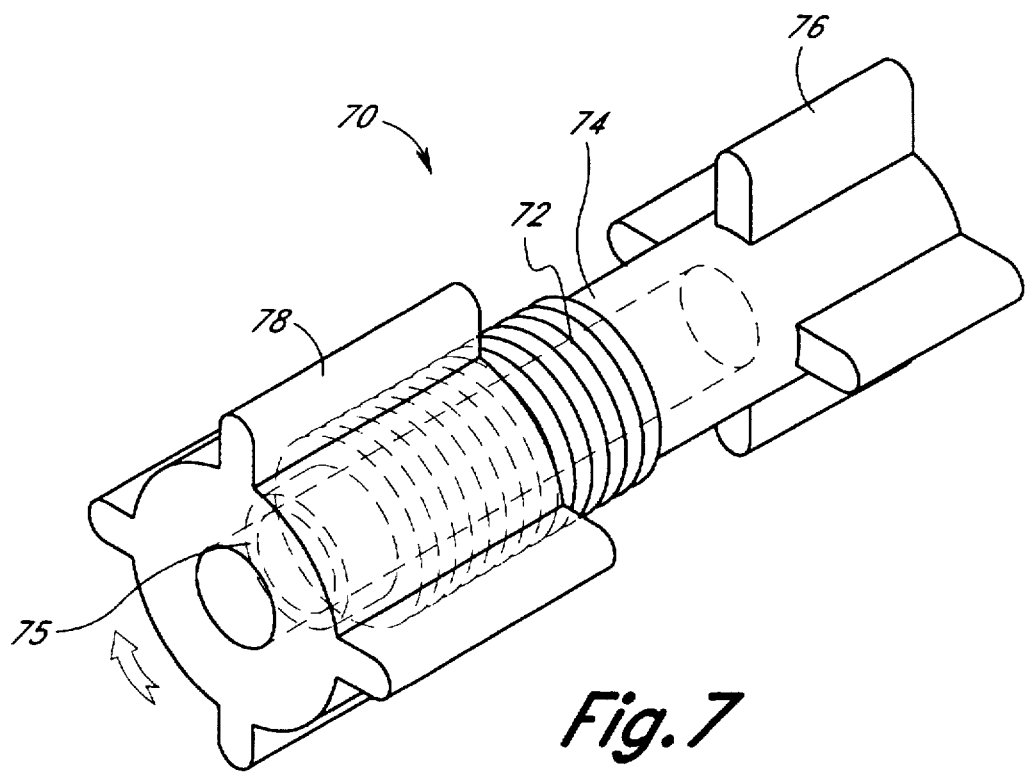

FIG. 1 shows a lattice-like stent 20 prior to positioning around a distal end 21 of a commercially available balloon delivery catheter 22 to form a stent-balloon assembly 24. The assembly 24 may be used in a percutaneous transluminal angioplasty (PTA) procedure, or the assembly 24 may be used in surgical procedures of other body lumens. A balloon 26 of the catheter may be formed of polyvinyl chloride (PVC) or polyethylene terephthalate (PET), for example, and may be of any type having the uninflated and inflated diameters desired for use with a particular patient. A guidewire 28 is typically used with the balloon catheter 22 and extends distally from the end of the balloon 26.

The stent 20 may be formed of stainless steel, or may other durable material suitable for implantation, as desired. Tantalum or even bioabsorbable materials may also be usable. The stent 20 may also be formed of a memory alloy, such as nitinol. It will be noted that the present invention is not limited to stents utilizing plastic deformation as its functionality, especially since almost all stents exhibit some recoil over time. Cross-pieces or struts (not shown) may be provided on the stent 20 which also expand upon inflation of the balloon 26 and ensure stability of the stent. The stent 20 may be manufactured as a flat, rectangular piece. In its initial or unexpanded state, the stent 20 is preferably rolled to have a double winding, and in its working or expanded state its longitudinal edges are substantially aligned.

Alternatively, the stent 20 may comprise a stainless steel slotted tube formed in two segments which are connected longitudinally and having a polygonal cross-section, such as a Palmaz-Schatz balloon-expandable stent available from Johnson and Johnson, New Brunswick, N.J. The unexpanded diameter of the stent may be 1.5 mm and the expanded diameter may be 5 mm, for example. Or, the stent may comprise a single strand of surgical suture wire made from stainless steel or tantalum, such as a Gianturco-Roubin stent available from Cook Inc., Bloomington, Ind. This stent is tooled into a balloon-expandable serpentine coil. Other commercially available stents, as well as other balloon catheters, are suitable for use with the present invention without loss of the benefits and advantages thereof; although, it should be noted that the present invention is compatible with other therapeutic devices which may be deployed by means other than balloon catheters.

Referring to FIG. 2, a preferred embodiment 30 of an apparatus having features of the present invention is shown prior to insertion of the stent-balloon assembly 24 within a first, inner member 32 of the apparatus. The assembly 24 may be moved toward the apparatus 30, as shown, or, alternatively, the apparatus 30 may be moved toward the assembly 24 for its insertion therein. A second, outer member 34 of the apparatus is positioned on the inner member 32 as provided by the manufacturer. Preferably, the inner and outer members 32, 34 have relatively large diameter flanges 36, 38 to facilitate grasping of the apparatus 30 and crimping of the stent 20 as described below.

In an apparatus and method of the present invention, the outer member 34 is slid longitudinally (to the right in FIG. 2) over the inner member 32 and a plurality protuberances or bumps 40 on a portion 42 of its exterior surface; although, they could also be placed on the interior surface 44 of the inner member 32, so long as the inner diameter of the outer member 34 was sized to cause compression of the inner member 32. The bumps 40 are preferably provided both longitudinally and circumferentially on the inner member 32 (see FIGS. 4 and 5). The portion 42 having the bumps 40 extends a length substantially overlying the length of the assembly 24 when placed within the inner member 32. As a result, as shown in a detail view in FIG. 3, the force of the outer member 34 as it slides over the inner member 32 compresses the bumps 40 radially inward such that the interior surface 44 of a channel 46 of the inner member 32 compresses the assembly 24, thereby crimping the stent 20 into position on the balloon 26. For purposes of this invention, the term "crimping" shall be construed broadly to an apparatus or method of positioning the stent on a deployment device. Thus, as illustrated in FIG. 3, depressions or deformations are noncontinuously formed on the exterior surface of the stent 20 which results in areas of reduced inner diameter of the stent wall.

Referring now to the exploded view of the apparatus 30 as shown in FIG. 4, its flange 36 is preferably provided at a proximal end of the inner or forming member 32, and a portion 48 of the inner member 32 adjacent a distal face 50 of the flange 36 has a substantially smooth exterior lacking any bumps 40. The central channel 46 is sized to readily receive the stent-balloon assembly 24 without its compression. As further shown in FIG. 5, the bumps 40 are preferably equally spaced around and along a majority of the length of the inner member 32, although the bumps 40 may be randomly or irregularly spaced, circumferentially as well as radially, on the inner member 32 in alternative embodiments. While the bumps 40 are shown as having rounded shapes, other shapes such as conical or pyramidal, for example, may also be used. Alternatively, the bumps 40 need not have smooth distal surfaces, but may have spiked or pointed tips, and may even have single or double prongs, in order to effect suitable forming and crimping actions upon the struts of a stent.

It should be noted that the forming member 32 need not be limited to positive bumps or protuberances on its exterior surface, but may also comprise positive protuberances placed on the interior surface wall of the channel 46 such that the protuberances directly engage the stent or engage it through some other protective means. In either event, the protuberances comprise forming devices which, when supplied with appropriate force, apply a crimping pressure to the stent. These crimping pressures may be supplied by any of a wide variety of pressure members and may be applied circumferentially, radially, linearly, or in any other patterned or random configuration. Also, the forming protuberances are not limited to placement on the forming member, but may also be placed on the pressure member, in which case two separate devices or components are not necessary, and a single integral device is provided. However, with respect to the embodiment illustrated in FIGS. 2–6, the forming protuberances are placed on the exterior surface of the inner member 32.

Thus, the inner or forming member 32 is comprised of a deformable material, such as a thermoplastic elastomer, styrene-ethylene butadiene-styrene block copolymer, or any suitable material known to those skilled in the art. The material provides a deformable wall of the channel 46 and allows radial compression of the bumps 40 into the channel, wherein the interior surface 44 transmits the compressive force from each bump 40 to the stent 20. Due to the fact that stents are typically not formed of a continuous section of material, and instead have openings between the struts thereof, a plurality of bumps 40 is desirable to ensure adequate points of compression along the length of the stent 20 onto the balloon 26. This is described below in more detail and illustrated in connection with FIGS. 14–16.

As an additional advantage of the present invention, the apparatus 30 may be disposable or re-usable. Thus, it may be possible to utilize a plastic or other material in the construction of the assembly which would allow the aforementioned deformation and compression of the stent 20 but which would later allow the assembly to be restored to its original arrangement having the bumps 40 on its exterior surface. This could be accomplished, for example, by use of a plunger or rod, having an outer diameter substantially the same as the original diameter of the channel, inserted into the channel 46 to provide a radially outward force on the channel wall.

Also shown in FIG. 4 is the outer or pressure member 34, which is shown in an end view in FIG. 6. Its flange 38 is preferably provided on a distal end. In alternative embodiments, the flange 38 may be replaced, for example, by an annular ring placed generally centrally along the length of the outer member 34, or, the outer member 34 could comprise a substantially frusto-conical shape having its reduced outer diameter positioned adjacent the distal face 50 of the flange 36 of the inner member 32. A separation of the flanges 36, 38, or grasping surfaces, of the inner and outer members 32, 34 is desirable to allow ready separation and movement of the outer member 34 with respect to the inner member 32.

A central channel 52 extends along the longitudinal axis of the outer member 34. Preferably, distal and proximal ends 54, 56 of the channel 52 are chamfered to facilitate the sliding of the outer member 34 over the bumps 40 of the inner member 32. Alternatively, only the distal end 54 of the channel 52 may be chamfered.

The outer member 34 may be formed of any suitably rigid material, such as steel or a rigid thermoplastic known to those skilled in the art. The outer member 34 may be formed as a single piece and slid into position over the inner member 32. Alternatively, the outer member 34 may be formed in two symmetric halves which are assembled together by the manufacturer over the smooth portion 48 of the inner member 32. A press-fit of one or more tabs on each half of the outer member 34 may be provided, or alternative methods of assembling the outer member 34 over the inner member 32 may be utilized, as desired.

In the example of FIGS. 4–6, the relative dimensions of the inner and outer members 32, 34 may be as follows: The overall length of the inner member 32 is 1.530", the flange thickness is 0.100", the smooth portion 48 of the inner member 32 is 0.600", and the longitudinal separation of the tops of adjacent bumps 40 is 0.080". The flange diameter is 0.750", the maximum diameter formed by the bumps around the inner member 32 is 0.198", the outer diameter of the smooth portion 48 of the inner member 32 is 0.154", and the diameter of the channel 46 is 0.098". Thus, the present dimensions are suitable for a stent-balloon assembly 24 having an outer diameter of up to about 0.096" or 2.5 mm.

Preferably, the overall length of the outer member 34 is 0.460", the flange thickness is 0.100", the flange diameter is 0.750", the outer diameter of the rest of the outer member 34 is 0.358", and the diameter of the channel 52 is 0.156". Thus, the outer member 34 has a clearance of about 0.001", or one mil, between it and the outer surface of the smooth portion 48 of the inner member 32.

Preferably, a pressure of at least two atmospheres is applied by the present apparatus to the stent for its secure attachment to the balloon; however, even lower forces can result in noticeable deformation in the stent, thus providing some degree of crimping. Generally, local pressures above about 6 atmospheres will result in damage to the stent and/or balloon and should be avoided. That is, pressures which exceed the yield stress or the ultimate tensile strength of the balloon will result in damage and should be avoided.

As noted above, the present invention is not limited to the embodiment of FIGS. 2-6. In fact, other embodiments described below achieve the crimping advantages of the present invention, whether utilizing a uniform or non-uniform crimping pressure (which depends on whether or not forming protuberances or other forming devices are used).

Thus, FIG. 7 shows an alternative embodiment 70 of a stent positioning apparatus having features of the present invention. An elastomeric tube 72 having a stent-balloon assembly (not shown) contained in its longitudinal channel is placed within a first member 74 of the apparatus 70 having a recess 75 at one end and exterior gripping fins 76 at the other, closed end. The recess 75 is sized to closely receive the tube 72 without compression and extends a length less than the tube length. The exterior of the first member 74 overlying the recess 75 is threaded to engage a second member comprising a nut 78. Rotation of the nut 78 for its engagement onto the first member 74 causes compression of the tube 72, and thus compression of the stent-balloon assembly.

Figure 8:
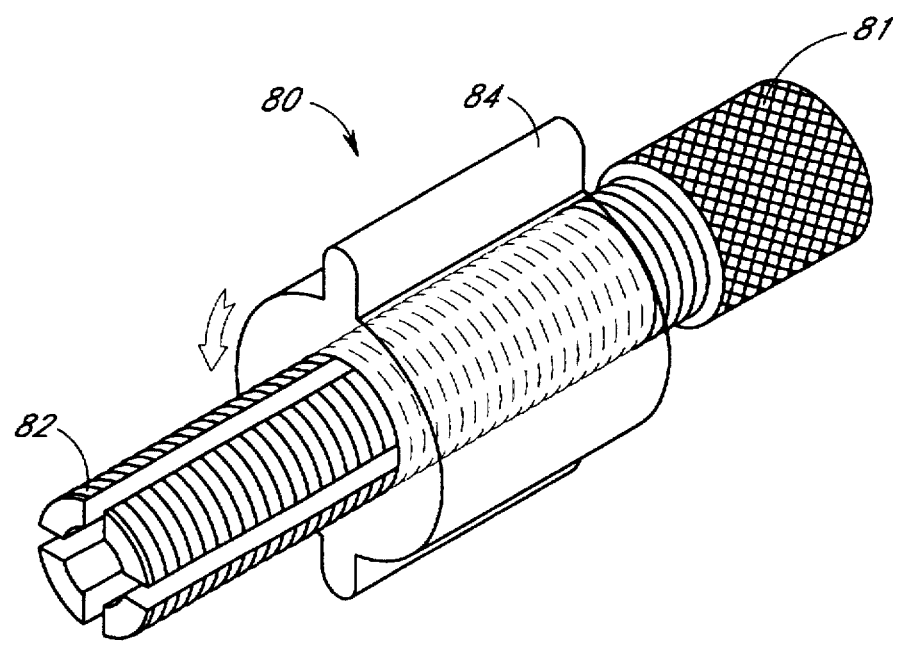

FIG. 8 shows another embodiment 80 of an apparatus having features of the present invention and comprises a threaded tube 82 which is quartered along substantially its entire length. A flange or handle 81 is provided at an end which is not divided into four quadrants. The major diameter of the thread increases along the length of the tube 82, such that when a nut 84 is rotatably engaged with the threaded tube 82, the inner diameter of the tube 82 is compressed. A stent-balloon assembly (not shown) contained within the tube 82 would thus be compressed as the nut 84 is rotated over the length of the assembly. It will be noted that the embodiments of FIGS. 7 and 8 may be utilized with forming devices (such as protuberances) formed on the inner surface of the forming members, or may be used without such forming devices in order to provide a uniform circumferential crimping pressure.

FIG. 9 shows another embodiment 90 comprising a plurality of disks 92 attached to and spaced along the length of a spring 94 which is formed into a circle. The circle is secured by superpositioning of coils at the ends of the spring 94, or by soldering or the like. The disks 92 have central openings sized for an interference fit with the outer diameter of the spring 94 and are preferably equidistantly spaced around the circle formed by the spring 94. The spring 94 and disks 92 are rolled along the length of a stent-balloon assembly 96 to provide the required compressive force for crimping the stent, the disk 92, providing a type of non-uniform, non-continuous crimping on the stent. The apparatus 90 may be applied directly to the stent-balloon assembly 96, or to a protective sleeve 98 placed around the assembly 96, as shown. Due to the elastic nature of the spring 94 in the circular arrangement, the apparatus 90 may be used with stent-balloon assemblies of various diameters, as desired, with any additional compressive force required for the smaller assembly diameters being provided by the person using the apparatus.

FIGS. 10 and 11 show other alternative embodiments 100, 110, wherein an elastic circular member 114 is applied to a stent-balloon assembly 102 preferably having a protective sleeve 104. In FIG. 10, the member is a coil-type spring 114 without the disks 92 of the previous embodiment 90, and in FIG. 11, the member is an O-ring 115. As with the previous embodiment, radial compression is achieved by rolling of the circular member 104, 114 over the length of the assembly 102 in the sleeve 104. In each of the foregoing embodiments of an apparatus having features of the present invention, the radial compression and crimping of the stent is achieved by forces applied longitudinally along the stent-balloon assembly.

Referring now to FIG. 12, an alternative embodiment 120 of an apparatus of the present invention is shown comprising a braided tube 122 having flanges 124, 125 at its ends. Preferably, the tube 122 is formed of stainless steel and is provided by the manufacturer having a first length and diameter. Upon the separation or relative movement of the flanges 124, 125 away from each other as indicated by the arrows, the tube 122 increases in length and decreases in diameter. Thus, a substantially uniform, radially compressive force is applied to a stent-balloon assembly (not shown) contained within the tube 122.

Figure 13:
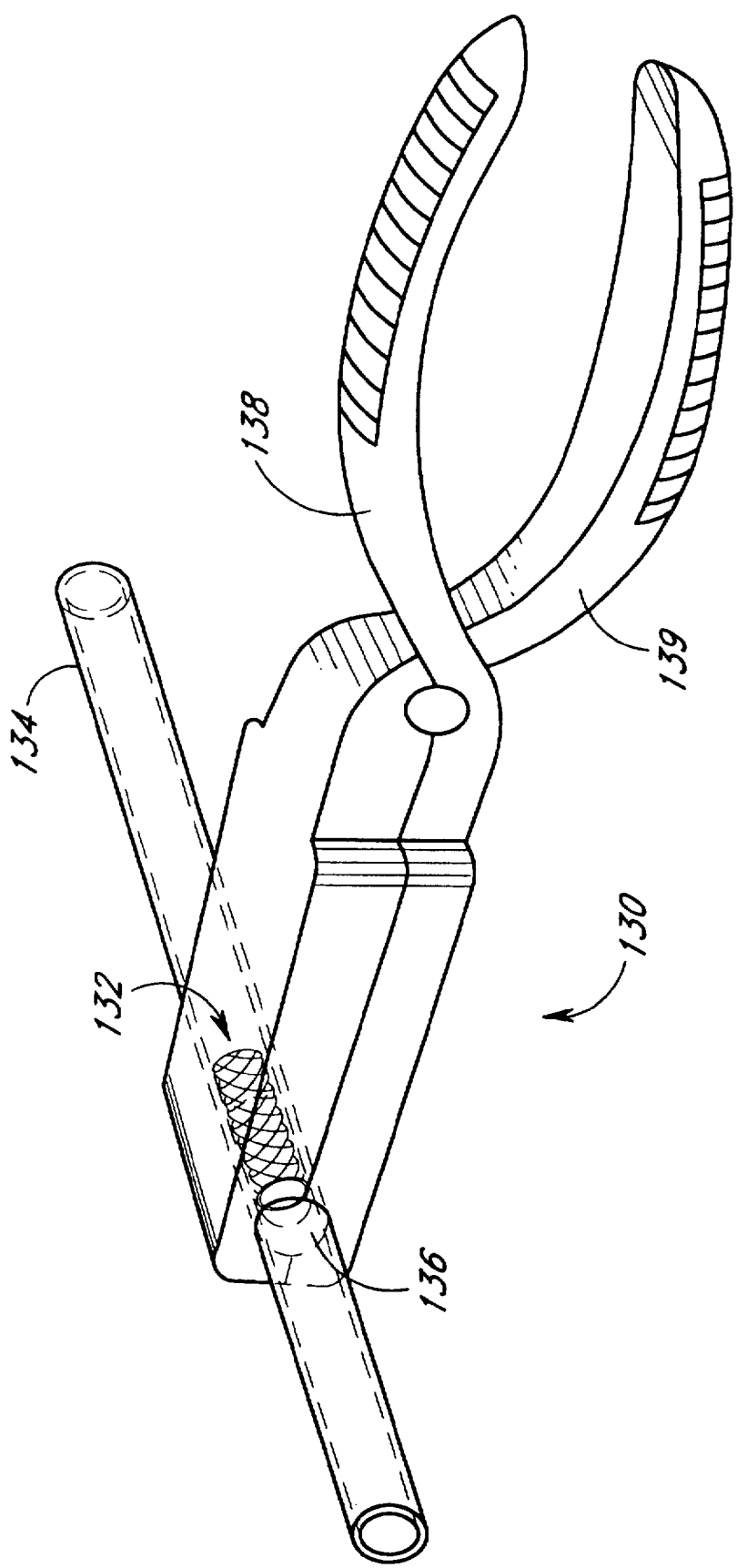

FIG. 13 shows yet another embodiment 130 of an apparatus of the present invention, comprising a pliers-like tool which is applied either directly to a stent-balloon assembly 132 or over a protective sleeve 134 surrounding the assembly, as shown. A distal end of the tool 130 has mating transverse grooves 136 formed on two halves 138, 139 of the tool. The grooves 136 form a diameter substantially the desired "crimped diameter" of the stent. Application of the force to compress the stent is easily accomplished by one hand of the user; however, due to the sizing of the distal end, the user is prevented from applying excessive pressure to the stent. A plurality of tools 130 visibly marked with the appropriate crimped diameter may be provided to the physician for ready access in the operating room.

The embodiments of FIGS. 12 and 13 illustrate devices in which an integral crimping mechanism is provided. That is, the stent can be received into a channel or other receptacle of the forming member and then crimped to the deployment device by the same apparatus. Thus, it will be understood that the principles of the present invention are not limited to any particular arrangement of forming protuberances or pressure members.

As noted above, the present invention is compatible with current stent design and construction. Advantageously, the use of forming devices such a protuberances avoid damage to the stent by randomly or selectively deforming its struts in only certain localized areas. Thus, there is a more secure attachment with less risk of damage to both the stent as well as the deployment device. These advantages are illustrated in more detail in FIGS. 14 and 15.

Figure 14:
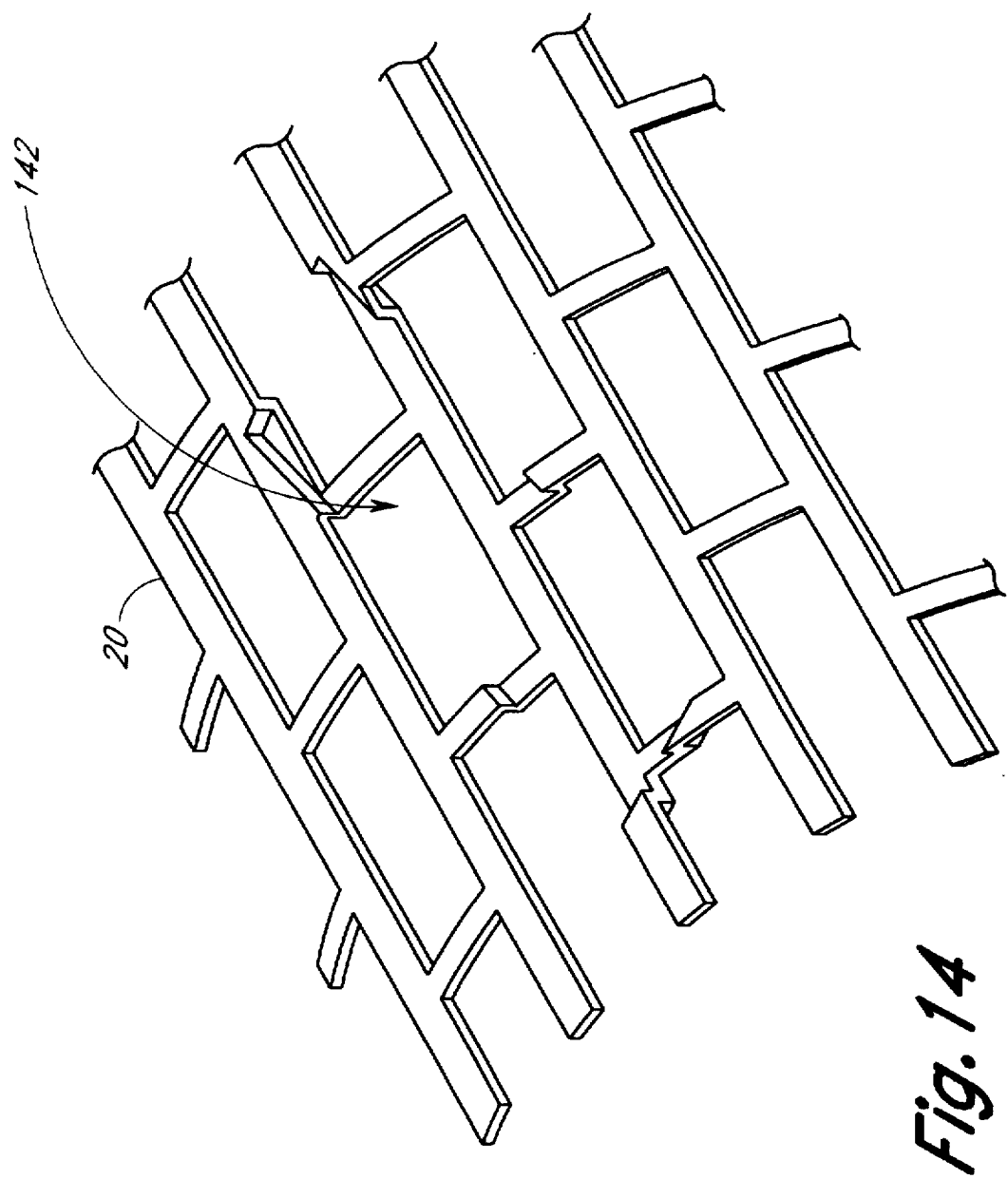
FIGS. 14–16 show perspective detail views of alternative arrangements of depressions.
Figure 15:
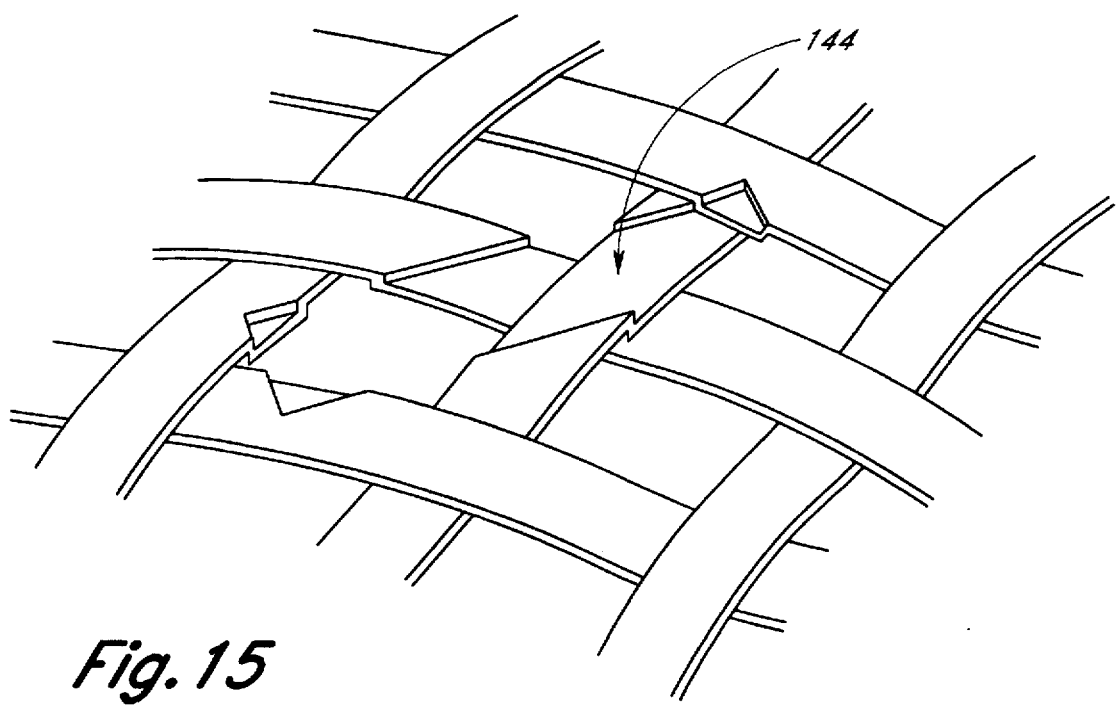

FIGS. 14 and 15 illustrate additional possible arrangements for the depressions formed during the crimping of the stent.

In particular, FIG. 14 illustrates a commonly used stent 20 in its pre-dilated configuration. This figure shows a single depression 142 formed by a device configured for rectangular-shaped depressions. FIG. 15 shows, with respect to a different stent, a single depression 144 formed by a similar rectangular device.

Figure 16:
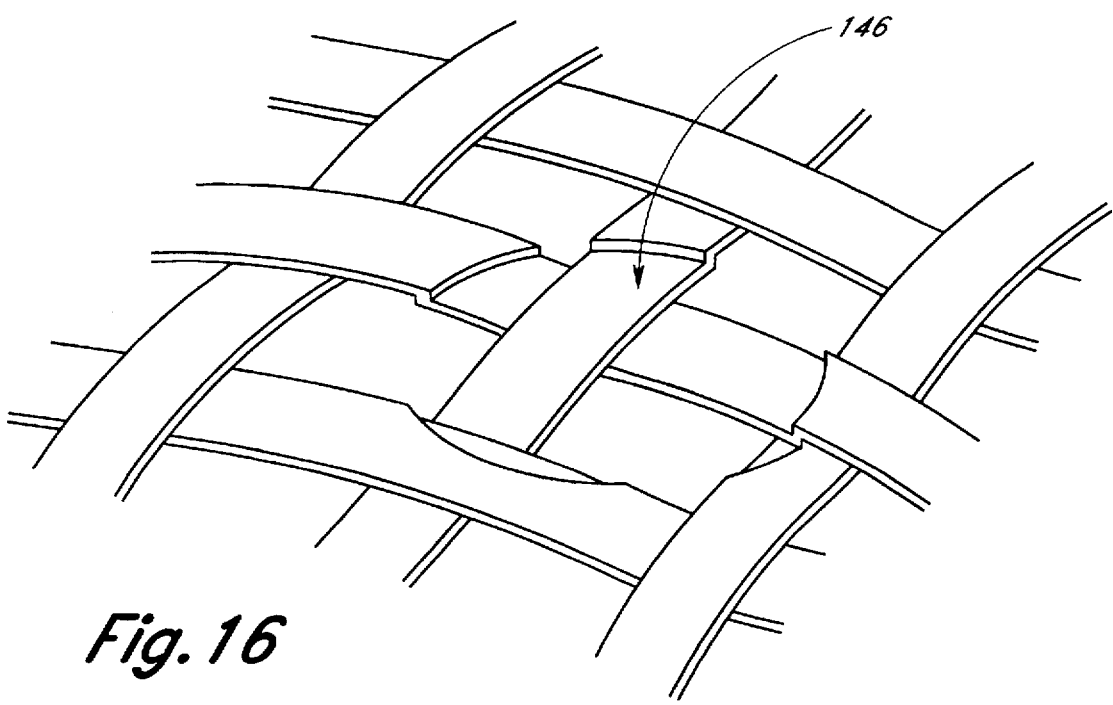

FIG. 16 illustrates a depression 146 having an oval shaped crimping depression, which could be somewhat similar to that formed by the protuberances of the apparatus 20 shown in FIGS. 2–6. In each case, each depression covers an area which includes a plurality of the struts or filaments of the stent. The depth of the depression may be substantially uniform, as shown, or, alternatively, the depth may vary over the depressed area. The edges of the depression may be sharp, as shown, or rounded. Moreover, it would be noted that the stents shown in FIGS. 14, 15 and 16 are schematic only, in order to illustrate the general nature of the depressions formed by the apparatus and method of the present invention, which, as described above, is compatible with virtually any stent configuration.

The apparatus and method of the present invention as disclosed herein may be used for grafts or other prostheses requiring similar application of compressive forces for their attachment. The present invention is not limited to use with stent-balloon assemblies, and may be used to prepare tools used for other body lumens.

Furthermore, the embodiments described above are provided merely to illustrate the present invention. Changes and modifications may be made from the embodiments presented herein by those skilled in the art without departure from the spirit and scope of the invention, as defined by the appended claims.

What is claimed is:

1. An apparatus for securing a therapeutic device, such as a stent and the like, onto a distal end of a deployment device, said therapeutic device having predetermined inner and outer diameters, said apparatus comprising:
   a first member having a radially deformable wall defining a channel along its longitudinal axis, said first member having a plurality of forming members thereon, said channel having a diameter greater than said outer diameter of said therapeutic device such that said therapeutic device and said deployment device are positionable within said channel; and
   a second member having an opening for receiving said first member, said first member insertable within said opening, said second member applying a crimping pressure on said first member such that said forming members on said first member reduces the inner diameter of said therapeutic device nonuniformly, thereby securing said therapeutic device onto said deployment device for positioning within a patient during a surgical procedure said forming members adapted to produce noncontinuous depressions in said therapeutic device to prevent both longitudinal and rotational relative movement between said therapeutic device and said deployment device.

2. The apparatus of claim 1, wherein said first member further comprises forming devices for receiving the crimping pressure applied by said second member and transmitting it to said therapeutic device.

3. The apparatus of claim 2, wherein said forming devices comprise protuberances formed on said first member.

4. The apparatus of claim 2, wherein said protuberances are generally spherical in shape.

5. The apparatus of claim 2, wherein said protuberances are generally frustroconical in shape.

6. The apparatus of claim 2, wherein said protuberances are formed on the outer surface of said first member.

7. The apparatus of claim 2, wherein said protuberances are formed on said channel.

8. The apparatus of claim 2, wherein said protuberances are randomly placed on said first member.

9. The apparatus of claim 2, wherein said protuberances are selectively placed on said first member.

10. The apparatus of claim 2, wherein said protuberances are noncontinuously placed on said first member.

11. The apparatus of claim 6, wherein said protuberances have a maximum outer diameter which is greater than the opening of said second member.

12. The apparatus of claim 11, wherein said second member is slidable relative to said first member, whereby said protuberances interfere with said opening of said second member to provide said crimping pressure.

13. An apparatus for securing a therapeutic device, such as a stent, and the like, onto a deployment device, said therapeutic device being dimensioned so as to be positionable over said deployment device, said apparatus comprising:
   an inner member comprising a first channel and a plurality of forming members placed on said inner member, said first channel defining an opening dimensioned to receive said therapeutic device and said deployment device, said forming members being noncontinuously placed on said inner member; and
   an outer member comprising a second channel dimension to receive said inner member, said outer member slidable relative to said inner member, said second channel and said forming members cooperating to apply a nonuniform crimping force on said therapeutic device to produce one or more depressions in said therapeutic device, whereby said therapeutic device is secured to said deployment device.

14. The apparatus of claim 13, wherein said forming members are placed on the outer surface of said inner member.

15. The apparatus of claim 13, wherein said forming members are placed on the inner surface of said first channel.

16. The apparatus of claim 13, wherein said outer member is manually slidable with respect to said inner member.

17. The apparatus of claim 13, wherein said forming members and said second channel provide an interference fit.

18. The apparatus of claim 13, wherein said apparatus is nonmanually operated.

19. An apparatus for securing a therapeutic device on a deployment device, comprising:
   an inner member comprising a channel and at least one forming member, said channel dimensioned to receive such therapeutic and said deployment devices; and
   a pressure member for applying a crimping pressure on said forming member to selectively deform said therapeutic device, said forming members adapted to produce continuous depressions in said therapeutic device whereby said therapeutic device is secured on said deployment device.

20. The apparatus of claim 19, wherein said inner member and said pressure member comprise separate components.

21. The apparatus of claim 19, wherein said pressure member comprises a circumferential spring for applying a radial crimping pressure on said forming member.

22. The apparatus of claim 19, wherein said pressure member comprises a longitudinal spring.

23. The apparatus of claim 19, wherein said pressure member comprises a threaded fitting.

24. The apparatus of claim 19, wherein said forming member is placed on the inner surface of said channel.

25. An apparatus for securing a therapeutic device on a deployment device, comprising:
   a channel dimensioned to receive said therapeutic device and said deployment device;
   forming means placed on said channel so as to be adjacent said therapeutic device, said forming means being arranged on said channel so as to be noncontinuous with respect to the outer surface of said therapeutic device; and
   pressure means for applying a crimping pressure on said forming means to selectably deform said therapeutic device to produce noncontinuous depressions in said therapeutic device, whereby said therapeutic device is secured on said deployment device.

26. A method for securing a therapeutic device, such as a stent and the like, on a deployment device, comprising:
   a. positioning the therapeutic device over the deployment device;
   b. placing a plurality of forming members adjacent to the therapeutic device; and
   c. applying a force to the forming members to cause them to engage the therapeutic device and selectively form the therapeutic device to produce noncontinuous depressions in said therapeutic device, such that said therapeutic device engages the deployment device in a crimping manner, but substantially solely in the locations of said forming members.

27. The method of claim 26, wherein said forming members comprise protuberances.

28. The method of claim 26, wherein said force is applied radially with respect to said therapeutic device.

29. The method of claim 26, wherein said force is applied longitudinally with respect to said therapeutic device.

30. The method of claim 26, wherein the step of placing the forming members adjacent to the therapeutic device comprises the step of placing the forming members noncontinuously with respect to the outer surface of said therapeutic device.

31. The method of claim 26, further comprising the step of selecting the shape of said forming members from a variety of forming shapes.

32. The apparatus of claim 25, wherein said forming means comprise protuberances to produce said depressions.

33. The apparatus of claim 32, wherein said protuberances are generally spherical in shape.

34. The apparatus of claim 32, wherein said protuberances are generally frustroconical in shape.

35. The apparatus of claim 32, wherein said protuberances are randomly distributed on said forming means.

36. An apparatus comprising:
   a therapeutic device having predetermined inner and outer diameters;
   a deployment device;
   a first member having a radially deformable wall defining a channel along its longitudinal axis, said first member having a plurality of forming members thereon, said channel having a diameter greater than said outer diameter of said therapeutic device such that said device and said deployment device are positionable within said channel; and
   a second member having an opening for receiving said first member, said first member insertable within said opening, said second member applying a crimping pressure on said first member such that said forming members on said first member reduces the inner diameter of said therapeutic device nonuniformly, thereby securing said therapeutic device onto said deployment device for positioning within a patient during a surgical procedure said forming members adapted to produce noncontinuous depressions in said therapeutic device to prevent both longitudinal and rotational relative movement between said therapeutic device and said deployment device.

37. The apparatus of claim 36, wherein said therapeutic device is a stent.

38. The apparatus of claim 36, wherein said deployment device is a catheter.

39. The apparatus of claim 36, wherein said forming members comprise protuberances.

* * * * *